(12) United States Patent
Cheng et al.

(10) Patent No.: US 7,858,832 B2
(45) Date of Patent: *Dec. 28, 2010

(54) PROCESS FOR PRODUCING PHENOL AND METHYL ETHYL KETONE

(75) Inventors: Jane C. Cheng, Bridgewater, NJ (US); John S. Buchanan, Lambertville, NJ (US); Jon E. Stanat, Houston, TX (US); Christine N. Elia, Bridgewater, NJ (US); Jihad M. Dakka, Whitehouse Station, NJ (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/162,958

(22) PCT Filed: Feb. 8, 2007

(86) PCT No.: PCT/EP2007/001209

§ 371 (c)(1),
(2), (4) Date: Oct. 27, 2008

(87) PCT Pub. No.: WO2007/093361

PCT Pub. Date: Aug. 23, 2007

(65) Prior Publication Data

US 2009/0312580 A1  Dec. 17, 2009

Related U.S. Application Data

(60) Provisional application No. 60/773,015, filed on Feb. 14, 2006.

(51) Int. Cl.
*C07C 15/067* (2006.01)
*C07C 45/53* (2006.01)
*C07C 37/08* (2006.01)

(52) U.S. Cl. ............... 585/446; 585/467; 568/385; 568/768; 568/798

(58) Field of Classification Search ............... 568/385, 568/768, 798; 585/461, 467
See application file for complete search history.

(56) References Cited

U.S. PATENT DOCUMENTS

| 4,992,606 A | 2/1991 | Kushnerick et al. | 525/467 |
| 5,059,736 A * | 10/1991 | Tamura et al. | 585/461 |
| 5,557,024 A | 9/1996 | Cheng et al. | 585/467 |
| 6,717,025 B1 * | 4/2004 | Risch et al. | 585/804 |
| 6,720,462 B2 * | 4/2004 | Kuhnle et al. | 568/768 |
| 2004/0059167 A1 | 3/2004 | Clark et al. | 585/446 |
| 2008/0086018 A1 | 4/2008 | Cheng et al. | 568/365 |

FOREIGN PATENT DOCUMENTS

| WO | 02/088051 | 11/2002 |
| WO | 2006/015826 | 2/2006 |

OTHER PUBLICATIONS

Yen, "Phenol," *Process Economics Program Report No. 22B: Phenol Supplement B*, Stanford Research Institute, pp. 113-121, 261 and 263 (1977).

* cited by examiner

*Primary Examiner*—Sikarl A Witherspoon
(74) *Attorney, Agent, or Firm*—Jamie Sullivan

(57) ABSTRACT

A process for producing sec-butylbenzene comprises contacting a feed comprising benzene and a $C_4$ alkylating agent under alkylation conditions comprising a temperature of about 110° C. to about 150° C. with a catalyst comprising at least one molecular sieve having an X-ray diffraction pattern including d-spacing maxima at 12.4±0.25, 6.9±0.15, 3.57±0.07 and 3.42±0.07 Angstrom. The sec-butylbenzene can be then oxidized to produce a hydroperoxide and the hydroperoxide decomposed to produce phenol and methyl ethyl ketone.

24 Claims, No Drawings

PROCESS FOR PRODUCING PHENOL AND METHYL ETHYL KETONE

CROSS REFERENCE TO RELATED PATENT APPLICATIONS

This application is a national stage filing of International Patent Cooperation Treaty Application No. PCT/EP2007/001209, filed Feb. 8, 2007, which claims priority from U.S. Ser. No. 60/773,015, filed Feb. 14, 2006, the disclosure of which is fully incorporated herein by reference.

FIELD

The present invention relates to a process for producing sec-butylbenzene and for converting the sec-butylbenzene to phenol and methyl ethyl ketone.

BACKGROUND

Phenol and methyl ethyl ketone are important products in the chemical industry. For example, phenol is useful in the production of phenolic resins, bisphenol A, ε-caprolactam, adipic acid, alkyl phenols, and plasticizers, whereas methyl ethyl ketone can be used as a lacquer, a solvent and for dewaxing of lubricating oils.

The most common route for the production of methyl ethyl ketone is by dehydrogenation of sec-butyl alcohol (SBA), with the alcohol being produced by the acid-catalyzed hydration of butenes. For example, commercial scale SBA manufacture by reaction of butylene with sulfuric acid has been accomplished for many years via gas/liquid extraction.

Currently, the most common route for the production of phenol is the Hock process. This is a three-step process in which the first step involves alkylation of benzene with propylene to produce cumene, followed by oxidation of the cumene to the corresponding hydroperoxide and then cleavage of the hydroperoxide to produce equimolar amounts of phenol and acetone. However, the world demand for phenol is growing more rapidly than that for acetone. In addition, the cost of propylene relative to that for butenes is likely to increase, due to a developing shortage of propylene. Thus, a process that uses butenes instead of propylene as feed and coproduces methyl ethyl ketone rather than acetone may be an attractive alternative route to the production of phenol.

It is known that phenol and methyl ethyl ketone can be co-produced by a variation of the Hock process in which sec-butylbenzene is oxidized to obtain sec-butylbenzene hydroperoxide and the peroxide decomposed to the desired phenol and methyl ethyl ketone. An overview of such a process is described in pages 113-121, 261 and 263 of Process Economics Report No. 22B entitled "Phenol," published by the Stanford Research Institute in December 1977.

Sec-butylbenzene can be produced by alkylating benzene with n-butenes over an acid catalyst. The chemistry is very similar to ethylbenzene and cumene production. However, as the carbon number of the alkylating agent increases, the number of product isomers also increases. For example, ethylbenzene has one isomer, propylbenzene has two isomers (cumene and n-propylbenzene), and butylbenzene has four isomers (n-, iso-, sec-, and t-butylbenzene). For sec-butylbenzene production, it is important to minimize n-, iso-, t-butylbenzene, and phenylbutenes by-product formation. These by-products, especially iso-butylbenzene, have boiling points very close to sec-butylbenzene and hence are difficult to separate from sec-butylbenzene by distillation (see table below).

| Butylbenzene | Boiling Point, ° C. |
|---|---|
| t-Butylbenzene | 169 |
| i-Butylbenzene | 171 |
| s-Butylbenzene | 173 |
| n-Butylbenzene | 183 |

Moreover, isobutylbenzene and tert-butylbenzene are known to be inhibitors to the oxidation of sec-butylbenzene to the corresponding hydroperoxide, a necessary next step for the production of methyl ethyl ketone and phenol.

It is also desirable to reduce other by-products such as butene oligomers, dibutylbenzenes and tributylbenzenes. These by-products consume butene and benzene feed and compromise sec-butylbenzene selectivity. The olefinic butene oligomers can also have an inhibiting effect on sec-butylbenzene oxidation rates.

Moreover, although sec-butylbenzene production can be maximized by using a pure n-butene feed, it is desirable to employ more economical butene feeds, such as Raffinate-2. A typical Raffinate-2 contains 0-1% butadiene and 0-5% isobutene. With this increased isobutene in the feed, a higher t-butylbenzene make is expected, which further increases the importance of the sec-butylbenzene selectivity of the catalyst. In our International Application No. PCT/EP2005/008557, filed Aug. 5, 2005, we have described an integrated process for producing phenol and methyl ethyl ketone, the process comprising (a) contacting a feed comprising benzene and a $C_4$ alkylating agent under alkylation conditions with a catalyst comprising zeolite beta or an MCM-22 family zeolite to produce an alkylation effluent comprising sec-butylbenzene; (b) oxidizing the sec-butylbenzene to produce a hydroperoxide; and then (c) cleaving the hydroperoxide to produce phenol and methyl ethyl ketone. The alkylation conditions include a temperature of about 60° C. to about 260° C., for example about 100° C. to about 200° C., with all the Examples being conducted at 160° C.

In accordance with the present invention, surprisingly it has now been found that if the alkylation process described in our International Application No. PCT/EP2005/008557 is conducted with the temperature controlled within narrowly defined limits of about 110° C. to about 150° C., then the selectivity to sec-butylbenzene is significantly increased over operation at higher temperatures without excessive loss in the activity of the catalyst. Since the alkylation product is substantially free of isobutylbenzene and tert-butylbenzene, it is an attractive feed for use in the Hock process to produce phenol and methyl ethyl ketone. It is known from, for example, U.S. Pat. No. 4,992,606 that MCM-22 is an effective catalyst for alkylation of aromatic compounds, such as benzene, with alkylating agents, such as olefins, having from 1 to 5 carbon atoms over a wide range of temperatures from about 0° C. to about 500° C., preferably from about 50° C. and about 250° C. Similar disclosures are contained in U.S. Pat. Nos. 5,371,310 and 5,557,024 but where the zeolite is MCM-49 and MCM-56 respectively. However, there is no disclosure or suggestion in these references that MCM-22, MCM-49 or MCM-56 should be unusually selective to sec-butylbenzene in the alkylation of benzene with a $C_4$ alkylating agent, particularly when the alkylation process is conducted at a temperature of about 110° C. to about 150° C.

SUMMARY

In one aspect, the present invention resides in a process for producing sec-butylbenzene, the process comprising contacting a feed comprising benzene and a $C_4$ alkylating agent under alkylation conditions comprising a temperature of about 110° C. to about 150° C. with a catalyst comprising at least one molecular sieve having an X-ray diffraction pattern including d-spacing maxima at 12.4±0.25, 6.9±0.15, 3.57±0.07 and 3.42±0.07 Angstrom.

Preferably, the molecular sieve is selected from MCM-22, MCM-49, MCM-56 and isotypes thereof, and more preferably from MCM-49, MCM-56 and isotypes thereof. Conveniently, said alkylation conditions comprise a temperature of about 120° C. to about 140° C., preferably about 125° C. to about 135° C.

Conveniently, the $C_4$ alkylating agent in (a) comprises a linear butene, for example 1-butene and/or 2-butene. In one embodiment, said linear butene is contained in a mixed $C_4$ stream which is subjected to at least one of sulfur removal, nitrogen removal, oxygenate removal, butadiene removal and isobutene removal prior to the contacting (a). Conveniently, said mixed $C_4$ stream is a Raffinate-1 or a Raffinate-2 stream.

In one embodiment, said contacting is conducted under at least partial liquid phase conditions. Conveniently, said alkylation conditions also include a pressure of 7000 kPa or less, and a feed weight hourly space velocity (WHSV) based on $C_4$ alkylating agent of from about 0.1 to 50 $hr^{-1}$ and a molar ratio of benzene to $C_4$ alkylating agent from about 1 to 50.

In one embodiment, said alkylation effluent produced in (a) comprises polybutylbenzenes and the process further comprises contacting said polybutylbenzenes with benzene in the presence of a transalkylation catalyst to produce sec-butylbenzene. Conveniently, the transalkylation catalyst comprises a molecular sieve selected from zeolite beta, mordenite, USY, MCM-22, PSH-3, SSZ-25, ERB-1, ITQ-1, ITQ-2, MCM-36, MCM-49, MCM-56, UZM-8, and mixtures thereof.

In a further aspect, the present invention resides in a process for producing phenol and methyl ethyl ketone, the process comprising:

(a) contacting a feed comprising benzene and a $C_4$ alkylating agent under alkylation conditions comprising a temperature of about 110° C. to about 150° C. with a catalyst comprising at least one molecular sieve having an X-ray diffraction pattern including d-spacing maxima at 12.4±0.25, 6.9±0.15, 3.57±0.07 and 3.42±0.07 Angstrom to produce an alkylation effluent comprising sec-butylbenzene;

(b) oxidizing the sec-butylbenzene from (a) to produce a hydroperoxide; and (c) cleaving the hydroperoxide from (b) to produce phenol and methyl ethyl ketone.

Conveniently, the oxidizing (b) is conducted in the presence of a catalyst, such as a catalyst selected from (i) an oxo (hydroxo) bridged tetranuclear metal complex comprising manganese, (ii) an oxo (hydroxo) bridged tetranuclear metal complex having a mixed metal core, one metal of the core being a divalent metal selected from Zn, Cu, Fe, Co, Ni, Mn and mixtures thereof and another metal being a trivalent metal selected from In, Fe, Mn, Ga, Al and mixtures thereof and (iii) an N-hydroxy substituted cyclic imide either alone or in the presence of a free radical initiator. In one embodiment, the oxidization catalyst is a heterogeneous catalyst.

Conveniently, the oxidizing (b) is conducted at a temperature of about 70° C. to about 200° C. and a pressure of about 0.5 to about 10 atmospheres (50 to 1000 kPa).

Conveniently, the cleaving (c) is conducted in the presence of a catalyst. The catalyst can be a homogeneous or hetergeneous catalyst. In one embodiment, the catalyst is a homogeneous catalyst, such as sulfuric acid.

Conveniently, the cleaving (c) is conducted at a temperature of about 40° C. to about 120° C., a pressure of about 100 to about 2500 kPa, and a liquid hourly space velocity (LHSV) based on the hydroperoxide of about 0.1 to about 100 $hr^{-1}$.

DETAILED DESCRIPTION OF THE EMBODIMENTS

The present invention is directed to a process for producing sec-butylbenzene and then converting the sec-butylbenzene to phenol and methyl ethyl ketone. The conversion involves initially oxidizing the sec-butylbenzene to produce the corresponding hydroperoxide and then cleaving the resulting hydroperoxide to produce the desired phenol and methyl ethyl ketone.

In particular, the invention is based on the discovery that when benzene is alkylated with a $C_4$ alkylating agent, such as a mixed butene feed, over a catalyst comprising a molecular sieve of the MCM-22 family, preferably MCM-49, MCM-56 and/or an isotype thereof and the alkylation temperature is controlled within narrowly defined limits of about 110° C. to about 150° C., then the selectivity of the process to the production of sec-butylbenzene is unexpectedly enhanced over a process using the same catalyst but at a temperature of 160° C. or above. Below 110° C., the rate of conversion of the butene feed becomes undesirably low.

Benzene Alkylation

The benzene employed in the alkylation step to produce sec-butylbenzene can be any commercially available benzene feed, but preferably the benzene has a purity level of at least 99 wt %.

The alkylating agent can be any aliphatic or aromatic organic compound having one or more available alkylating aliphatic groups capable of reaction with benzene and having 4 carbon atoms. Examples of suitable $C_4$ alkylating agents include monoolefins, such as linear butenes, particularly butene-1 and/or butene-2; alcohols (inclusive of monoalcohols, dialcohols, trialcohols, etc.) such as the butanols; dialkyl ethers, such as dibutyl ethers; and alkyl halides such as the butyl chlorides.

The alkylating agent can also be an olefinic $C_4$ hydrocarbon mixture such as can be obtained by steam cracking of ethane, propane, butane, LPG and light naphthas, catalytic cracking of naphthas and other refinery feedstocks and by conversion of oxygenates, such as methanol, to lower olefins.

For example, the following $C_4$ hydrocarbon mixtures are generally available in any refinery employing steam cracking to produce olefins; a crude steam cracked butene stream, Raffinate-1 (the product remaining after solvent extraction or hydrogenation to remove butadiene from the crude steam cracked butene stream) and Raffinate-2 (the product remaining after removal of butadiene and isobutene from the crude steam cracked butene stream). Generally, these streams have compositions within the weight ranges indicated in Table A below.

TABLE A

| Component | Crude C$_4$ stream | Raffinate 1 | | Raffinate 2 | |
|---|---|---|---|---|---|
| | | Solvent Extraction | Hydrogn. | Solvent Extraction | Hydrogn. |
| Butadiene | 30-85% | 0-2% | 0-2% | 0-1% | 0-1% |
| C4 acetylenes | 0-15% | 0-0.5% | 0-0.5% | 0-0.5% | 0-0.5% |
| Butene-1 | 1-30% | 20-50% | 50-95% | 25-75% | 75-95% |
| Butene-2 | 1-15% | 10-30% | 0-20% | 15-40% | 0-20% |
| Isobutene | 0-30% | 0-55% | 0-35% | 0-5% | 0-5% |
| N-butane | 0-10% | 0-55% | 0-10% | 0-55% | 0-10% |
| Iso-butane | 0-1% | 0-1% | 0-1% | 0-2% | 0-2% |

Other refinery mixed C$_4$ streams, such as those obtained by catalytic cracking of naphthas and other refinery feedstocks, typically have the following composition:

| | |
|---|---|
| Propylene | 0-2 wt % |
| Propane | 0-2 wt % |
| Butadiene | 0-5 wt % |
| Butene-1 | 5-20 wt % |
| Butene-2 | 10-50 wt % |
| Isobutene | 5-25 wt % |
| Iso-butane | 10-45 wt % |
| N-butane | 5-25 wt % |

C$_4$ hydrocarbon fractions obtained from the conversion of oxygenates, such as methanol, to lower olefins more typically have the following composition:

| | |
|---|---|
| Propylene | 0-1 wt % |
| Propane | 0-0.5 wt % |
| Butadiene | 0-1 wt % |
| Butene-1 | 10-40 wt % |
| Butene-2 | 50-85 wt % |
| Isobutene | 0-10 wt % |
| N- + iso-butane | 0-10 wt % |

Any one or any mixture of the above C$_4$ hydrocarbon mixtures can be used in the process of the invention. In addition to linear butenes and butanes, these mixtures typically contain components, such as isobutene and butadiene, which can be deleterious to the process of the invention. For example, the normal alkylation product of isobutene with benzene is tert-butylbenzene which, as previously stated, acts as an inhibitor to the subsequent oxidation step. Thus, prior to the alkylation step, these mixtures preferably are subjected to butadiene removal and isobutene removal. For example, isobutene can be removed by selective dimerization or reaction with methanol to produce MTBE, whereas butadiene can be removed by extraction or selective hydrogenation to butene-1.

In addition to other hydrocarbon components, commercial C$_4$ hydrocarbon mixtures typically contain other impurities which could be detrimental to the alkylation process. For example, refinery C$_4$ hydrocarbon streams typically contain nitrogen and sulfur impurities, whereas C$_4$ hydrocarbon streams obtained by oxygenate conversion processes typically contain unreacted oxygenates and water. Thus, prior to the alkylation step, these mixtures may also be subjected to one or more of sulfur removal, nitrogen removal and oxygenate removal, in addition to butadiene removal and isobutene removal. Removal of sulfur, nitrogen, oxygenate impurities is conveniently effected by one or a combination of caustic treatment, water washing, distillation, adsorption using molecular sieves and/or membrane separation. Water is also typically removed by adsorption.

Although not preferred, it is also possible to employ as the alkylating agent in the alkylation step of the invention a mixture of a C$_4$ alkylating agent, as described above, and C$_3$ alkylating agent, such as propylene, so that the alkylation step produces a mixture of cumene and sec-butylbenzene. The resultant mixture can then be processed through oxidation and cleavage, to make a mixture of acetone and MEK, along with phenol, preferably where the molar ratio of acetone to phenol is 0.5:1, to match the demand of bisphenol-A production.

Conveniently, the total feed to the alkylation step of the present invention contains less than 1000 ppm, such as less than 500 ppm, for example less than 100 ppm, water. In addition, the total feed typically contains less than 100 ppm, such as less than 30 ppm, for example less than 3 ppm, sulfur and less than 10 ppm, such as less than 1 ppm, for example less than 0.1 ppm, nitrogen.

The alkylation catalyst used in the present process is a crystalline molecular sieve having an X-ray diffraction pattern including d-spacing maxima at 12.4±0.25, 6.9±0.15, 3.57±0.07 and 3.42±0.07 Angstrom. The X-ray diffraction data used to characterize the material (b) are obtained by standard techniques using the K-alpha doublet of copper as the incident radiation and a diffractometer equipped with a scintillation counter and associated computer as the collection system.

Materials having the above X-ray diffraction pattern are sometimes referred to as molecular sieves of the MCM-22 family and include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), MCM-36 (described in U.S. Pat. No. 5,250,277), MCM-49 (described in U.S. Pat. No. 5,236,575), MCM-56 (described in U.S. Pat. No. 5,362,697), UZM-8 (described in U.S. Pat. No. 6,756,030), and mixtures thereof. Preferably, the molecular sieve is selected from (a) MCM-49, (b) MCM-56 and (c) isotypes of MCM-49 and MCM-56, such as ITQ-2.

The term "MCM-22 family material" (or "material of the MCM-22 family" or "molecular sieve of the MCM-22 family"), as used herein, includes one or more of:

molecular sieves made from a common first degree crystalline building block unit cell, which unit cell has the MWW framework topology. (A unit cell is a spatial arrangement of atoms which if tiled in three-dimensional space describes the crystal structure. Such crystal structures are discussed in the "Atlas of Zeolite Framework Types", Fifth edition, 2001, the entire content of which is incorporated as reference);

molecular sieves made from a common second degree building block, being a 2-dimensional tiling of such MWW framework topology unit cells, forming a monolayer of one unit cell thickness, preferably one c-unit cell thickness;

molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks can be in a regular fashion, an irregular fashion, a random fashion, or any combination thereof, and molecular sieves made by any regular or random 2-dimensional or 3-dimensional combination of unit cells having the MWW framework topology.

The alkylation catalyst can include the molecular sieve in unbound or self-bound form or, alternatively, the molecular sieve can be combined in a conventional manner with an oxide binder, such as alumina, such that the final alkylation catalyst contains between 2 and 80 wt % sieve.

In one embodiment, the catalyst is unbound and has a crush strength much superior to that of catalysts formulated with binders. Such a catalyst is conveniently prepared by a vapor phase crystallization process, in particular a vapor phase crystallization process that prevents caustic used in the synthesis mixture from remaining in the zeolite crystals as vapor phase crystallization occurs.

The alkylation process is conducted such that the organic reactants, i.e., the alkylatable aromatic compound and the alkylating agent, are brought into contact with an alkylation catalyst in a suitable reaction zone such as, for example, in a flow reactor containing a fixed bed of the catalyst composition or in a catalytic distillation reactor, under effective alkylation conditions. Most importantly, the alkylation conditions include a temperature of from about 110° C. to about 150° C., for example about 120° C. to about 140° C., such as about 125° C. to about 135° C., typically about 130° C. In addition, the alkylation conditions generally include a pressure of 7000 kPa or less, for example from about 1000 to about 3500 kPa, and a weight hourly space velocity (WHSV) based on $C_4$ alkylating agent of between about 0.1 and about 50 $hr^{-1}$, for example between about 1 and about 10 $hr^{-1}$. Typically, the molar ratio of benzene to alkylating agent is from about 1 to about 50, for example from about 2 to about 10.

The reactants can be in either the vapor phase or partially or completely in the liquid phase and can be neat, i.e., free from intentional admixture or dilution with other material, or they can be brought into contact with the zeolite catalyst composition with the aid of carrier gases or diluents such as, for example, hydrogen or nitrogen.

Using the catalyst and alkylation temperature described above, it is found that the alkylation step of the process of the invention is highly selective to sec-butylbenzene. In particular, it is found that the sec-butylbenzene produced normally contains less than 0.5 wt % of isobutylbenzene or tert-butylbenzene even using a mixed butene feed such as Raffinate-2. This is very advantageous, because oxidation of sec-butylbenzene is affected by the presence of iso-butylbenzene and tert-butylbenzene, a significant reduction in the sec-butylbenzene oxidation rate occurring when these impurities exceed 0.7 wt % of the sec-butylbenzene feed. Although the alkylation step is highly selective towards sec-butylbenzene, the effluent from the alkylation reaction will normally contain some polyalkylated oligomerization products, as well as unreacted aromatic feed and the desired monoalkylated species. The unreacted aromatic feed is normally recovered by distillation and recycled to the alkylation reactor. The bottoms from the benzene distillation are further distilled to separate monoalkylated product from any polyalkylated products and other heavies. Depending on the amount of polyalkylated products present in the alkylation reaction effluent, it may be desirable to transalkylate the polyalkylated products with additional benzene to maximize the production of the desired monoalkylated species. Transalkylation with additional benzene is typically effected in a transalkylation reactor, separate from the alkylation reactor, over a suitable transalkylation catalyst, such as a molecular sieve of the MCM-22 family, zeolite beta, MCM-68 (see U.S. Pat. No. 6,014,018), zeolite Y and mordenite. Molecular sieves of the MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), MCM-36 (described in U.S. Pat. No. 5,250,277), MCM-49 (described in U.S. Pat. No. 5,236,575), MCM-56 (described in U.S. Pat. No. 5,362,697), UZM-8 (described in U.S. Pat. No. 6,756,030), and mixtures thereof. The transalkylation reaction is typically conducted under at least partial liquid phase conditions, which suitably include a temperature of 100 to 300° C., a pressure of 1000 to 7000 kPa, a weight hourly space velocity of 1 to 50 $hr^{-1}$ on total feed, and a benzene/polyalkylated benzene weight ratio of 1 to 10.

Sec-Butyl Benzene Oxidation

In order to convert the sec-butylbenzene into phenol and methyl ethyl ketone, the sec-butylbenzene is initially oxidized to the corresponding hydroperoxide. This is accomplished by introducing an oxygen-containing gas, such as air, into a liquid phase containing the sec-butylbenzene. The reaction can be performed in the absence of a catalyst but is slow (of the order of <1%/hour at 100 psig (698.5 kPag) pressure). Improvement in the reaction rate can be achieved by performing the oxidation in the presence of a catalyst, such as a water-soluble chelate compound in which multidentate ligands are coordinated to at least one metal from cobalt, nickel, manganese, copper, and iron. (See U.S. Pat. No. 4,013,725). More preferably, a heterogeneous catalyst is used. Suitable heterogeneous catalysts are described in U.S. Pat. No. 5,183,945, wherein the catalyst is an oxo (hydroxo) bridged tetranuclear manganese complex and in U.S. Pat. No. 5,922,920, wherein the catalyst comprises an oxo (hydroxo) bridged tetranuclear metal complex having a mixed metal core, one metal of the core being a divalent metal selected from Zn, Cu, Fe, Co, Ni, Mn and mixtures thereof and another metal being a trivalent metal selected from In, Fe, Mn, Ga, Al and mixtures thereof. The entire disclosures of said U.S. patents are incorporated herein by reference.

Other suitable catalysts for the sec-butylbenzene oxidation step are the N-hydroxy substituted cyclic imides described in Published U.S. Patent Application No. 2003/0083527 and incorporated herein by reference, such as N-hydroxyphthalimide, 4-amino-N-hydroxyphthalimide, 3-amino-N-hydroxyphthalimide, tetrabromo-N-hydroxyphthalimide, tetrachloro-N-hydroxyphthalimide, N-hydroxyhetimide, N-hydroxyhimimide, N-hydroxytrimellitimide, N-hydroxybenzene-1,2,4-tricarboximide, N,N'-dihydroxy(pyromellitic diimide), N,N'-dihydroxy(benzophenone-3,3',4,4'-tetracarboxylic diimide), N-hydroxymaleimide, pyridine-2,3-dicarboximide, N-hydroxysuccinimide, N-hydroxy(tartaric imide), N-hydroxy-5-norbornene-2,3-dicarboximide, exo-N-hydroxy-7-oxabicyclo [2.2.1]hept-5-ene-2,3-dicarboximide, N-hydroxy-cis-cyclohexane-1,2-dicarboximide, N-hydroxy-cis-4-cyclohexene-1,2 dicarboximide, N-hydroxynaphthalimide sodium salt or N-hydroxy-o-benzenedisulphonimide. These materials can be used either alone or in the presence of a free radical initiator and can be used as liquid-phase, homogeneous catalysts or can be supported on a solid carrier to provide a heterogeneous catalyst.

Suitable conditions for the sec-butylbenzene oxidation step include a temperature between about 70° C. and about 200° C., such as about 90° C. to about 130° C., and a pressure of about 0.5 to about 10 atmospheres (50 to 1000 kPa). A basic buffering agent may be added to react with acidic by-products that may form during the oxidation. In addition, an aqueous phase may be introduced, which can help dissolve basic compounds, such as sodium carbonate. The per-pass conversion in the oxidation step is preferably kept below 50%, to minimize the formation of byproducts. The oxidation reaction is conveniently conducted in a catalytic distillation unit and the sec-butylbenzene hydroperoxide produced may be concentrated by distilling off the unreacted sec-butylbenzene prior to the cleavage step.

Hydroperoxide Cleavage

The final step in the conversion of the sec-butylbenzene into phenol and methyl ethyl ketone involves cleavage of the sec-butylbenzene hydroperoxide, which is conveniently effected by contacting the hydroperoxide with a catalyst in the liquid phase at a temperature of about 20° C. to about 150° C., such as about 40° C. to about 120° C., a pressure of about 50 to about 2500 kPa, such as about 100 to about 1000 kPa and a liquid hourly space velocity (LHSV) based on the hydroperoxide of about 0.1 to about 100 $hr^{-1}$, preferably about 1 to about 50 $hr^{-1}$. The sec-butylbenzene hydroperoxide is preferably diluted in an organic solvent inert to the cleavage reaction, such as methyl ethyl ketone, phenol or sec-butylbenzene, to assist in heat removal. The cleavage reaction is conveniently conducted in a catalytic distillation unit.

The catalyst employed in the cleavage step can be a homogeneous catalyst or a heterogeneous catalyst.

Suitable homogeneous cleavage catalysts include sulfuric acid, perchloric acid, phosphoric acid, hydrochloric acid and p-toluenesulfonic acid. Ferric chloride, boron trifluoride, sulfur dioxide and sulfur trioxide are also effective homogeneous cleavage catalysts. The preferred homogeneous cleavage catalyst is sulfuric acid A suitable heterogeneous catalyst for use in the cleavage of sec-butylbenzene hydroperoxide includes a smectite clay, such as an acidic montmorillonite silica-alumina clay, as described in U.S. Pat. No. 4,870,217, the entire disclosure of which is incorporated herein by reference.

The following Examples are given for illustrative purposes and do not limit the scope of the invention.

EXAMPLE 1 (COMPARATIVE)

Sec-Butylbenzene Synthesis Using MCM-49 at 160° C.

A 0.5 gram sample of an MCM-49 catalyst (1.3 mm [1/20"] quadrulobe extrudate of 60% MCM-49/40% Versal 200 alumina binder, cut to 1.3 mm [1/20"] length) was used for the alkylation of benzene with a mixed butene feed having the following composition: 53.4% cis-butene, 41.2% trans-butene, 4.6% isobutene, 0.5% butadiene, 0.1% n-butane and 0.2% others. The catalyst was diluted with sand to 3 cc and loaded into an isothermal, down-flow, fixed-bed, tubular reactor having an outside diameter of 4.76 mm (3/16"). The catalyst was dried at 150° C. and 1 atm with 100 cc/min flowing nitrogen for 2 hours. The nitrogen was turned off and benzene was fed to the reactor at 60 cc/hr until the reactor pressure increased to 300 psig (2170 kPa). Benzene flow was then reduced to 7.63 cc/hr (6.67 WHSV) and the mixed butene feed was introduced from a syringe pump at 2.57 cc/hr. The reactor temperature was adjusted to 160° C. Feed benzene/butene molar ratio was maintained at 3:1 for the entire run. Liquid product was collected in a cold-trap and analyzed off line. Butene conversion was determined by measuring unreacted butene relative to feed butene. The MCM-49 was on stream for 3 days at 3.2 WHSV of butene with 96% conversion, 1 day at 9.6 WHSV with 80-83% conversion, and 3 days at 3.2 WHSV with 95% conversion. Relative activity of MCM-49 based on first-order butene conversion was 1.1. Representative data are shown in Table 1.

TABLE 1 sec-Butylbenzene Production with MCM-49 and Mixed Butene Feed at 160° C.

| Days on Stream | 2.3 | 3.2 | 5.3 |
|---|---|---|---|
| Butene WHSV, $h^{-1}$ | 3.2 | 9.6 | 3.2 |
| 2-Butene Conv, % | 96.1 | 83.0 | 95.5 |
| Isobutene Conv, % | 97.7 | 67.2 | 92.8 |
| Butadiene Conv, % | 100.0 | 100.0 | 100.0 |
| Product Selectivity, wt % | | | |
| i-$C_4$ | 0.041 | 0.032 | 0.028 |
| $C_5$-$C_7$ | 0.527 | 0.503 | 0.583 |
| $C_8$ and $C_{12}$ (butene oligomers) | 7.688 | 9.732 | 8.185 |
| Cumene | 0.128 | 0.144 | 0.127 |
| t-Butylbenzene | 1.849 | 0.849 | 1.240 |
| iso-Butylbenzene* | 0.000 | 0.008 | 0.012 |
| sec-Butylbenzene | 82.977 | 84.284 | 84.720 |
| n-Butylbenzene | 0.062 | 0.059 | 0.068 |
| Di-butylbenzene | 5.431 | 3.878 | 4.273 |
| Tri-butylbenzene | 1.079 | 0.429 | 0.629 |
| Heavies | 0.218 | 0.082 | 0.134 |
| Sum | 100.0 | 100.0 | 100.0 |
| Butylbenzene Composition, % | | | |
| t-Butylbenzene | 2.179 | 0.996 | 1.441 |
| iso-Butylbenzene* | 0.000 | 0.010 | 0.013 |
| sec-Butylbenzene | 97.749 | 98.925 | 98.467 |
| n-Butylbenzene | 0.073 | 0.069 | 0.078 |
| Sum | 100.0 | 100.0 | 100.0 |

*iso-Butylbenzene less than 0.5% in total butylbenzene not detectable with GC used.

EXAMPLE 2

Sec-Butylbenzene Synthesis Using MCM-49 at 130° C.

The process of Example 1 was repeated but using a 2.0 gram sample of the MCM-49 catalyst used in Example 1 and with the reactor temperature being adjusted to 130° C. and kept at 130° C. for the entire run. The catalyst was on stream for 8 days at 0.8 WHSV of butene with 94%+ 2-butene conversion, 1 day at 2.4 WHSV with 69-72% conversion. Relative activity of MCM-49 based on first-order butene conversion was 0.2. Representative data are shown in Table 2.

TABLE 2 sec-Butylbenzene Production with MCM-49 and Mixed Butene Feed at 130° C.

| Days on Stream | 4.8 | 6.8 | 8.8 |
|---|---|---|---|
| Butene WHSV, $h^{-1}$ | 0.8 | 0.8 | 2.4 |
| 2-Butene Conv, % | 96.3 | 95.7 | 71.3 |
| Isobutene Conv, % | 94.9 | 93.8 | 62.9 |
| Butadiene Conv, % | 100.0 | 100.0 | 100.0 |
| Product Selectivity, wt % | | | |
| i-$C_4$ | 0.008 | 0.004 | 0.004 |
| $C_5$-$C_7$ | 0.311 | 0.289 | 0.311 |
| $C_8$ and $C_{12}$ (butene oligomers) | 7.328 | 7.313 | 10.574 |
| Cumene | 0.030 | 0.028 | 0.072 |
| t-Butylbenzene | 0.403 | 0.358 | 0.212 |
| iso-Butylbenzene* | 0.000 | 0.000 | 0.000 |
| sec-Butylbenzene | 89.306 | 89.177 | 86.167 |
| n-Butylbenzene | 0.044 | 0.043 | 0.054 |

TABLE 2-continued sec-Butylbenzene Production with MCM-49
and Mixed Butene Feed at 130° C.

| Days on Stream | 4.8 | 6.8 | 8.8 |
|---|---|---|---|
| Di-butylbenzene | 2.290 | 2.500 | 2.344 |
| Tri-butylbenzene | 0.253 | 0.261 | 0.222 |
| Heavies | 0.027 | 0.027 | 0.040 |
| Sum | 100.0 | 100.0 | 100.0 |
| Butylbenzene Composition, % | | | |
| t-Butylbenzene | 0.449 | 0.399 | 0.245 |
| iso-Butylbenzene* | 0.000 | 0.000 | 0.000 |
| sec-Butylbenzene | 99.502 | 99.553 | 99.692 |
| n-Butylbenzene | 0.049 | 0.048 | 0.063 |
| Sum | 100.0 | 100.0 | 100.0 |

*iso-Butylbenzene less than 0.5% in total butylbenzene not detectable with GC used.

The data in Tables 1 and 2 show that the MCM-49 catalyst effectively alkylated benzene with the mixed butene feed with improved sec-butylbenzene selectivity when operated at 130° C., as compared with operation at 160° C. Table 3 provides a head-to-head comparison to demonstrate this improvement using data collected at 160° C. (Table 1) and data collected at 130° C. (Table 2). At comparable 2-butene conversion of 96%, operating MCM-49 at 130° C. vs. 160° C. shows clear advantages: sec-butylbenzene selectivity improved from 83-85% to 89%; whereas all by-product selectivities decreased.

TABLE 3

Comparison of MCM-49 Performance with Mixed
Butene Feed at Different Temperatures

| Temperature | 160° C. | 160° C. | 130° C. | 130° C. |
|---|---|---|---|---|
| Days on Stream | 2.3 | 5.3 | 4.8 | 6.8 |
| Butene WHSV, h$^{-1}$ | 3.2 | 3.2 | 0.8 | 0.8 |
| 2-Butene Conv, % | 96.1 | 95.5 | 96.3 | 95.7 |
| Isobutene Conv, % | 97.7 | 92.8 | 94.9 | 93.8 |
| Butadiene Conv, % | 100.0 | 100.0 | 100.0 | 100.0 |
| Product Selectivity, wt % | | | | |
| i-C$_4$ | 0.041 | 0.028 | 0.008 | 0.004 |
| C$_5$-C$_7$ | 0.527 | 0.583 | 0.311 | 0.289 |
| C$_8$ and C$_{12}$ (butene oligomers) | 7.688 | 8.186 | 7.328 | 7.313 |
| Cumene | 0.128 | 0.127 | 0.030 | 0.028 |
| t-Butylbenzene | 1.849 | 1.240 | 0.403 | 0.358 |
| iso-Butylbenzene* | 0.000 | 0.000 | 0.000 | 0.000 |
| sec-Butylbenzene | 82.977 | 84.730 | 89.306 | 89.177 |
| n-Butylbenzene | 0.062 | 0.068 | 0.044 | 0.043 |
| Di-butylbenzene | 5.431 | 4.273 | 2.290 | 2.500 |
| Tri-butylbenzene | 1.079 | 0.629 | 0.253 | 0.261 |
| Heavies | 0.218 | 0.134 | 0.027 | 0.027 |
| Sum | 100.0 | 100.0 | 100.0 | 100.0 |
| Butylbenzene Composition, % | | | | |
| t-Butylbenzene | 2.179 | 1.441 | 0.449 | 0.399 |
| iso-Butylbenzene* | 0.000 | 0.000 | 0.000 | 0.000 |
| sec-Butylbenzene | 97.749 | 98.480 | 99.502 | 99.553 |
| n-Butylbenzene | 0.073 | 0.079 | 0.049 | 0.048 |
| Sum | 100.0 | 100.0 | 100.0 | 100.0 |

*iso-Butylbenzene less than 0.5% in total butylbenzene not detectable with GC used.

EXAMPLE 3

Sec-Butylbenzene Synthesis Using MCM-22 at Different Temperatures

A 1.0 gram sample of an MCM-22 catalyst (1.6 mm [1/16"] diameter cylindrical extrudate of 65 wt % MCM-22/35% alumina binder cut to 1.6 mm [1/16"] length) was used for the alkylation of benzene with the mixed butene feed of Example 1 and according to the process of Example 1 (reactor temperature of 160° C.). The catalyst was on stream for 6 days at 1.6 WHSV of butene with 98% 2-butene conversion, 1 day at 4.8 WHSV with 80% conversion, 1 day at 7.2 WHSV with 62% conversion, and followed by 4 days again at 1.6 WHSV with 97% conversion. Representative data are shown in Table 4. Relative activity of MCM-22 based on first-order butene conversion was 0.5. A 2.3 gram sample of the same MCM-22 catalyst (65% MCM-22/35% alumina binder) was used for the alkylation of benzene with the mixed butene feed of Example 1 and according to the process of Example 2 (reactor temperature of 130° C.). The MCM-22 catalyst was on stream for 4 days at 0.43 WHSV of butene with 94%+2-butene conversion. Relative activity of MCM-22 based on first-order butene conversion was 0.1. Representative data are shown in Table 4, from which it will be seen that the sec-butylbenzene selectivity of the MCM-22 catalyst improved (from about 83 wt % to about 84 wt %) when operated at 130° C. as compared with operation at 160° C.

TABLE 4

Comparison of MCM-22 Performance with Mixed
Butene Feed at Different Temperatures

| Temperature | 160° C. | 160° C. | 130° C. | 130° C. |
|---|---|---|---|---|
| Days on Stream | 5.79 | 9.8 | 1.8 | 2.8 |
| Butene WHSV, h$^{-1}$ | 1.6 | 1.6 | 0.43 | 0.43 |
| 2-Butene Conv, % | 98.4 | 96.9 | 95.9 | 95.2 |
| Isobutene Conv, % | 96.8 | 93.7 | 99.5 | 98.6 |
| Butadiene Conv, % | 100.0 | 100.0 | 100.0 | 100.0 |
| Product Selectivity, wt % | | | | |
| i-C$_4$ | 0.034 | 0.027 | 0.016 | 0.012 |
| C$_5$-C$_7$ | 0.467 | 0.556 | 0.464 | 0.478 |
| C$_8$ and C$_{12}$ (butene oligomers) | 7.746 | 7.916 | 8.211 | 8.806 |
| Cumene | 0.189 | 0.196 | 0.048 | 0.048 |
| t-Butylbenzene | 1.521 | 1.267 | 0.839 | 0.613 |
| iso-Butylbenzene* | 0.000 | 0.000 | 0.000 | 0.000 |
| sec-Butylbenzene | 83.282 | 83.453 | 84.228 | 84.312 |
| n-Butylbenzene | 0.055 | 0.060 | 0.074 | 0.079 |
| Di-butylbenzene | 5.580 | 5.465 | 4.727 | 4.507 |
| Tri-butylbenzene | 0.926 | 0.837 | 0.985 | 0.806 |
| Heavies | 0.200 | 0.224 | 0.407 | 0.339 |
| Sum | 100.0 | 100.0 | 100.0 | 100.0 |
| Butylbenzene Composition, % | | | | |
| t-Butylbenzene | 1.792 | 1.494 | 0.985 | 0.721 |
| iso-Butylbenzene* | 0.000 | 0.000 | 0.000 | 0.000 |
| sec-Butylbenzene | 98.143 | 98.435 | 98.928 | 99.186 |
| n-Butylbenzene | 0.064 | 0.071 | 0.087 | 0.093 |
| Sum | 100.0 | 100.0 | 100.0 | 100.0 |

*iso-Butylbenzene less than 0.5% in total butylbenzene not detectable with GC used.

Based on available information, it is believed that MCM-56 and its isotypes will behave like MCM-49 and give significantly improved sec-butylbenzene selectivity when used to alkylate benzene with a C$_4$ alkylating agent under alkylation conditions comprising a temperature of about 110° C. to about 150° C.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

What is claimed is:

1. A process for producing sec-butyl benzene, the process comprising:

contacting a feed comprising benzene and a $C_4$ alkylating agent under alkylation conditions comprising a temperature of about 120° C. to about 140° C. with a catalyst comprising at least one molecular sieve having an X-ray diffraction pattern including d-spacing maxima at 12.4±0.25, 6.9±0.15, 3.57±0.07 and 3.42±0.07 Angstrom to form sec-butylbenzene wherein said contacting is conducted under at least partial liquid phase conditions.

2. The process of claim 1, wherein said at least one molecular sieve is selected from MCM-22, MCM-49, MCM-56 and isotypes thereof.

3. The process of claim 1, wherein said at least one molecular sieve is selected from MCM-49 and isotypes thereof.

4. The process of claim 1, wherein said alkylation conditions comprise a temperature of about 125° C. to about 135° C.

5. The process of claim 1, wherein said alkylation conditions also include a pressure of 7000 kPa or less, and a feed weight hourly space velocity (WHSV) based on $C_4$ alkylating agent of from about 0.1 to 50 $hr^{-1}$ and a molar ratio of benzene to $C_4$ alkylating agent from about 1 to about 50.

6. The process of claim 1, wherein said $C_4$ alkylating comprises a linear butene.

7. The process of claim 6, wherein said linear butene comprises 1-butene and or 2-butene.

8. The process of claim 6, wherein said linear butene is contained in a mixed $C_4$ stream.

9. The process of claim 8, wherein said mixed $C_4$ stream is derived from a steam-cracked crude $C_4$ stream comprising the following major components:

30 to 85 wt % butadiene
0 to 15 wt % C4 acetylenics
1 to 30 wt % butene-1
1 to 15 wt % butene-2
0 to 30 wt % isobutene
0 to 10 wt % normal-butane
0 to 1 wt % iso-butane.

10. The process of claim 8, wherein said mixed $C_4$ stream is derived from a raffinate stream obtained by subjecting a steam-cracked crude $C_4$ stream to a solvent extraction process to remove butadiene, wherein said raffinate stream comprises the following major components:

0 to 2 wt % butadiene
0 to 0.5 wt % C4 acetylenics
20 to 50 wt % butene-1
10 to 30 wt % butene-2
0 to 55 wt % isobutene
0 to 55 wt % normal-butane
0 to 1 wt % iso-butane.

11. The process of claim 8, wherein said mixed $C_4$ stream is derived from a raffinate stream obtained by subjecting a steam-cracked crude $C_4$ stream to reaction with methanol to remove isobutene, wherein said raffinate stream comprises the following major components:

0 to 2 wt % butadiene
0 to 0.5 wt % C4 acetylenics
50 to 95 wt % butene-1
0 to 20 wt % butene-2
0 to 35 wt % isobutene
0 to 10 wt % normal-butane
0 to 1 wt % iso-butane.

12. The process of claim 8, wherein said mixed $C_4$ stream is derived from a raffinate stream obtained by subjecting a steam-cracked crude $C_4$ stream to a solvent extraction process to remove butadiene and to a iso-butene removal process, wherein said raffinate stream comprises the following major components:

0 to 1 wt % butadiene
0 to 0.5 wt % C4 acetylenics
25 to 75 wt % butene-1
15 to 40 wt % butene-2
0 to 5 wt % isobutene
0 to 55 wt % normal-butane
0 to 2 wt % iso-butane.

13. The process of claim 8, wherein said mixed $C_4$ stream is derived from a raffinate stream obtained by subjecting a steam-cracked crude $C_4$ stream to a hydrogenation process to remove butadiene and to a iso-butene removal process, wherein said raffinate stream comprises the following major components:

0 to 1 wt % butadiene
0 to 0.5 wt % C4 acetylenics
75 to 95 wt % butene-1
0 to 20 wt % butene-2
0 to 5 wt % isobutene
0 to 10 wt % normal-butane
0 to 2 wt % iso-butane.

14. The process of claim 1 wherein the sec-butylbenzene produced from the contacting step (a) is oxidized at a temperature of about 70 to about 200° C. and a pressure of about 50 to about 1000 kPa in the presence of an N-hydroxy substituted cyclic imide and a basic buffering agent to produce a hydroperoxide.

15. The process of claim 14, wherein said refinery mixed butane/butene stream comprises the following major components:

| Propylene | 0-2 wt % |
|---|---|
| Propane | 0-2 wt % |
| Butadiene | 0-5 wt % |
| Butene-1 | 5-20 wt % |
| Butene-2 | 10-50 wt % |
| Isobutene | 5-25 wt % |
| Iso-butane | 10-45 wt % |
| N-butane | 5-25 wt %. |

16. The process of claim 8, wherein said mixed $C_4$ stream is derived from a $C_4$ fraction obtained from an oxygenate to olefin conversion process.

17. The process of claim 16, wherein said $C_4$ fraction comprises the following major components:

0 to 1 wt % propylene
0 to 0.5 wt % propane
0 to 1 wt % butadiene
10 to 40 wt % butene-1
50 to 85 wt % butene-2
0 to 10 wt % isobutene
0 to 10 wt % normal and isobutane.

18. A process for producing sec-butyl benzene, the process comprising contacting a feed comprising benzene and a $C_4$ alkylating agent under alkylation conditions comprising a temperature of about 120° C. to about 140° C. with a catalyst comprising at least one molecular sieve having an X-ray diffraction pattern including d-spacing maxima at 12.4±0.25, 6.9±0.15, 3.57±0.07 and 3.42±0.07 Angstrom to form sec-butylbenzene wherein said contacting is conducted at liquid phase conditions and wherein said mixed $C_4$ stream is derived from a raffinate stream obtained by subjecting a steam-cracked crude $C_4$ stream to a solvent extraction process to remove butadiene and to a iso-butene removal process.

19. The process of claim 8, wherein said mixed $C_4$ stream is subjected to at least one of sulfur removal, nitrogen removal, oxygenate removal, butadiene removal and isobutene removal prior to the contacting.

20. The process of claim 1, wherein the feed comprises at least one of (i) less than 1000 ppm water, (ii) less than 100 ppm sulfur and (iii) less than 10 ppm nitrogen.

21. The process of claim 1, wherein said contacting is conducted under liquid phase conditions.

22. The process of claim 1, wherein said contacting also produces polybutylbenzenes and the process further comprises contacting said polybutylbenzenes with benzene in the presence of a transalkylation catalyst to produce sec-butylbenzene.

23. The process of claim 22, wherein the transalkylation catalyst comprises a molecular sieve selected from zeolite beta, mordenite, USY, MCM-22, PSH-3, SSZ-25, ERB-1, ITQ-1, ITQ-2, MCM-36, MCM-49, MCM-56, UZM-8, and mixtures thereof

24. The process of claim 1, wherein the process produces a composition that is substantially free of iso-butylbenzene.

\* \* \* \* \*